United States Patent [19]

Heggie et al.

[11] Patent Number: 5,075,470

[45] Date of Patent: Dec. 24, 1991

[54] PROCESS FOR THE PREPARATION OF A RHODIUM COMPLEX

[75] Inventors: William Heggie, Barreiro; Philip R. Page, Sintra; Ivan Villax, Lisboa, all of Portugal; Indira Ghatak, London; Michael B. Hursthouse, Essex, both of England

[73] Assignee: Plurichemie Anstalt, Portugal

[21] Appl. No.: 558,058

[22] Filed: Jul. 26, 1990

[30] Foreign Application Priority Data

Jul. 31, 1989 [PT] Portugal ................................. 91333

[51] Int. Cl.$^5$ ............................................. C07F 15/00
[52] U.S. Cl. ................................... 556/137; 556/13; 556/19; 556/136; 502/155; 502/166
[58] Field of Search ................. 556/13, 16, 19, 136, 556/137; 552/204; 502/155, 166

[56] References Cited

U.S. PATENT DOCUMENTS

| | | | |
|---|---|---|---|
| Re. 32,535 | 10/1987 | Villax et al. | 502/166 X |
| 3,442,943 | 5/1969 | Marlell et al. | 260/559 |
| 3,484,483 | 12/1969 | Korst et al. | 260/559 |
| 3,755,194 | 8/1973 | Avilov et al. | 252/429 R |
| 4,031,137 | 6/1977 | Schmitt et al. | 260/559 AT |
| 4,190,595 | 2/1980 | Diamond et al. | 260/429 R |
| 4,743,699 | 5/1988 | Page et al. | 556/23 |
| 4,857,235 | 8/1989 | Heggie et al. | 556/21 X |
| 4,863,639 | 9/1989 | Heggie et al. | 502/166 X |
| 4,877,559 | 10/1989 | Page et al. | 552/204 |
| 4,911,865 | 3/1990 | Heggie et al. | 552/207 |
| 4,968,654 | 11/1990 | Heggie et al. | 502/166 |

FOREIGN PATENT DOCUMENTS

| | | |
|---|---|---|
| 668581 | 8/1963 | Canada . |
| 72435 | 7/1982 | European Pat. Off. . |
| 32257 | 2/1982 | Japan . |
| 1296340 | 11/1972 | United Kingdom . |

OTHER PUBLICATIONS

CA 78,97767b.
CA 95,214275d.
CA 90,104102j.

*Primary Examiner*—Arthur C. Prescott
*Attorney, Agent, or Firm*—Ostrolenk, Faber, Gerb & Soffen

[57] ABSTRACT

A process for the preparation of $\mu$-3-carbopentazane-$N^1$, $N^4$:$N^2$, $N^5$-bis-[bis(triphenylphosphine)rhodium (I)] dinitrate by the reaction of tris(triphenylphosphine)nitratorhodium (I) with hydrazine in degassed methanol under an inert atmosphere.

8 Claims, No Drawings

PROCESS FOR THE PREPARATION OF A RHODIUM COMPLEX

The present invention refers to a process for the preparation of $\mu$-3-carbopentazane-$N^1$, $N^4$:$N^2$,$N^5$-bis[bis(triphenylphosphine)rhodium (I)] dinitrate. This compound was previously described in European Patent Application No. 87 304 279.0 (Publication No. 0 283 616), wherein it was shown to be a stereospecific homogeneous hydrogenation catalyst, especially in the hydrogenation of the exocyclic methylene group of acid addition salts of 6-demethyl-6-deoxy-6-methylene-5-hydroxytetracycline (methacycline) to prepare $\alpha$-6-deoxy-5-hydroxytetracycline (doxycycline).

In European Patent Application No. 87 304 279.0 (Publication No. 0 283 616), the $\mu$-3-carbopentazane-$N^1$, $N^4$:$N^2$,$N^5$-bis[bis(triphenylphosphine)-rhodium (I)] dinitrate was prepared by the reaction of rhodium trinitrate dihydrate. hydrazine or hydrazine monohydrate and triphenylphosphine in methanol.

It has now been found that this compound can be prepared by reacting tris(triphenylphosphine)nitratorhodium (I) with hydrazine in methanol.

According to the present invention there is provided a process for the preparation of $\mu$-3-carbopentazane-$N^1$,$N^4$:$N^2$,$N^5$-bis[bis(triphenylphosphine)rhodium (I)] dinitrate, characterised by the fact that tris(triphenylphosphine)nitratorhodium (I) is reacted with hydrazine in degassed methanol under an inert atmosphere.

The starting material, tris(triphenylphosphine)nitratorhodium (I), has been described in British Patents Nos. 1,368,432 and 1,368,433. The preparation involved protonation of rhodium (II) acetate in methanol with 40% fluoroboric acid at 60° C. for about 16 hours. The resulting green solution was then treated with a saturated methanolic solution of triphenylphosphine to give an orange solid, identified as tris(triphenylphosphine)rhodium (I) fluoroborate. This was then reacted with lithium nitrate to give tris(triphenylphosphine)nitratorhodium (I), as a red solid with a melting point of 120° C.

Thus, the starting tris(triphenylphosphine)nitratorhodium (I) can be prepared by this process. Alternatively, it can be prepared by reacting at reflux 1 mole of rhodium trinitrate dihydrate with 6 moles of triphenylphosphine in ethanol or methanol.

In the case where the solvent was ethanol, the reaction time was 24 hours. A yellow precipitate was filtered off and the red filtrate was allowed to stand at room temperature. Red crystals were formed which were filtered and dried. The identity of the yellow precipitate was confirmed as

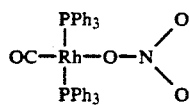

by X-ray crystallography.

The red crystals were shown to be

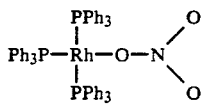

by X-ray crystallography and infra-red spectroscopy. The melting point was 120° C., identical with that quoted in British Patents Nos. 1,368,432 and 1 368,433.

In the case of methanol, the reaction time was much shorter, typically of the order of one hour. A first yellow precipitate was filtered off and the red filtrate was allowed to stand at room temperature. The red crystals so formed, were filtered and dried. The yellow microcrystalline precipitate has not been structurally identified. The red crystals have been confirmed to be tris(triphenylphosphine)nitratorhodium (I) by X-ray crystallography.

The conditions of preparation of $\mu$-3-carbopentazane-$N^1$,$N^4$:$N^2$,$N^5$-bis[bis(triphenylphosphine)rhodium (I)]-dinitrate are illustrated in Example 3.

The amount of hydrazine used was between 3 and 6 moles per mole of tris(triphenylphosphine)nitratorhodium (I), preferably between 4 and 5 moles.

The reactants were refluxed together overnight, preferably for 16 hours under an inert atmosphere, such as nitrogen. Upon standing, orange crystals were deposited, which were filtered off and dried under vacuum or under an inert atmosphere.

The identity was confirmed as $\mu$-3-carbopentazane-$N^1$,$N^4$:$N^2$,$N^5$-bis[bis(triphenylphosphine)rhodium (I)] dinitrate

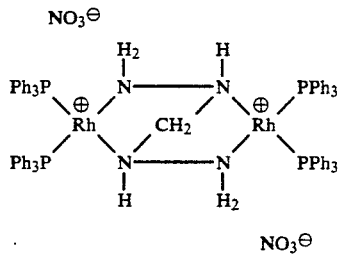

by X-ray crystallography. Additionally, the infra-red and nuclear magnetic resonance spectra were identical to those of the product obtained in European Patent Application No. 87 304 279.0 (publication no. 0 283 616).

The following examples serve to illustrate the invention, without in any way limiting the scope thereof.

EXAMPLE 1

Preparation of tris(triphenylphosphine)nitratorhodium (I) in ethanol

Rhodium trinitrate dihydrate (2.15 g; 7.02 mmoles as rhodium) was dissolved in 95% ethanol (60 ml), under a nitrogen atmosphere, in a two-necked round bottom flask. A hot solution of triphenylphosphine (10.51 g; 40.07 mmoles) in 95% ethanol (500 ml) was added. After refluxing under nitrogen for 24 hours, yellow triclinic crystals deposited in a deep red solution. These were filtered off and dried.

The found elemental analysis was C 61.98%; H 4.28%; N 1.80%; and P 9.42%. The infra-red spectrum showed a strong sharp peak at 1965cm$^{-1}$, indicative of the presence of a carbonyl group.

The compound was thus formulated as bis(triphenylphosphine)carbonyl-nitratorhodium (I), for which the calculated elemental analysis is C 61.94%; H 4.21%; N 1.95%; and P 8.63%. This formulation and a trans-phosphine structure was confirmed by X-ray crystallography.

The data for the crystal structure determination were collected using an Enraf-Nonis CAD4 diffractometer and graphite monochromated Mo-K$\alpha$ radiation, following standard procedures, solved and developed via standard heavy atom methods and refined by least squares. The details are as follows: $(Ph_3P)_2(CO)(NO_3)Rh$ : $C_{37}H_{40}O\ NP_2Rh$, Mol. wt.=717.52, triclinic, space group $\bar{P}1$, a=9.395(1), b=10.386(2), c=18.081(3)Å, $\alpha$=102.58(1), $\beta$=101.14(1), $\gamma$=89.95(1)°, V=1687.9 Å$^3$, Z=2, Dc=1.41 g.cm$^{-3}$, $\mu$(Mo-K$\alpha$)=6.28 cm$^{-1}$. The R value is currently 0.12 with disorder of the CO and NO$_3$ groups analogous to that found for the monoclinic form of the related carbonyl chloride complex complicating the refinement.

On standing, the red solution deposited red crystals which were identified by infra-red spectroscopy with sharp peaks at 1270 and 1000 cm$^{-1}$, indicative of a monodentate nitrate ligand, and X-ray crystallography to be tris(triphenylphosphine)nitratorhodium (I). The details of the latter, carried out as described above, are as follows: $(Ph_3P)_3(NO_3)Rh$ : $C_{54}H_{45}O_3NP_3Rh$. Mol. wt.=951.80, triclinic, space group $\bar{P}1$, a=10.506(1), b=12.187(2), c=18.420(2)Å, $\alpha$=87.56(2), $\beta$=77.75(2), $\gamma$=75.81(2)°, V=2234.3 Å$^3$, Z=2, Dc=1.414 g.cm$^{-3}$, $\mu$(Mo-K$\alpha$)=5.20 cm$^{-1}$. The R value is 0.0246 for 6702 data and 739 parameters.

EXAMPLE 2

Preparation of tris(triphenylphosphine)nitratorhodium (I) in methanol

Rhodium trinitrate dihydrate (0.215 g; 0.70 mmoles as rhodium) was dissolved, under a nitrogen atmosphere, in a two-necked round bottom flask, in the minimum quantity of methanol to give a clear solution. A hot solution of triphenylphosphine (1.051 g; 4.01 mmoles) in methanol (30 ml) was added. After refluxing under nitrogen for 1 hour, a yellow precipitate was deposited in a deep red solution. The precipitate was filtered off and, on standing, the red filtrate deposited red crystals, which were shown to be tris(triphenylphosphine)nitrtorhodium (I), identical with those obtained by the method given in Example 1.

EXAMPLE 3

Preparation of $\mu$-3-carbopentazane-N$^1$, N$^4$:N$^2$, N$^5$-bis[bis(triphenylphosphine)rhodium (I)] dinitrate Tris(triphenylphosphine)nitratorhodium (I) (0.20 g; 0.21 mmoles) and hydrazine (3.0 ml of a methanolic solution containing 1.00 ml/100 ml; 0.95 mmoles) were mixed in dry. degassed methanol (30 ml). The mixture was refluxed overnight (16 hours), and then cooled to room temperature. The orange crystals that formed were filtered and dried.

The identity of the crystals was checked by single crystal diffractometry. The unit cell dimensions found were:

a=12.878(2), b=23.925(3), c=24.441(4)Å, $\beta$=92.61(2)°, V=7522.7 Å$^3$.

In comparison, the full structure determination as described in European Patent Application No. 87 304 279.0 (publication no. 0 283 616) gave:

a=22.269(3), b=23.311(3), c=13.838(2)Å, $\beta$=100.51(2)°, V=7063.0 Å$^3$.

The infra-red and nuclear magnetic resonance spectra showed no discernible differences, thus suggesting that these crystals also were $\mu$-3-carbopentazane-N$^1$,N$^4$:N$^2$N$^5$-bis[bis (triphenylphosphine)rhodium (I)] dinitrate. This was confirmed by a full crystal structure analysis, following standard procedures, which showed that the difference lay in the number of molecules of methanol of crystallisation —three per complex unit in these new crystals, one per complex in the former.

We claim:

1. A process for the preparation of $\mu$-3-carbopentazane-N$^1$,N$^4$:N$^2$,N$^5$-bis-[bis (triphenylphosphine)rhodium (I)] dinitrate, characterised by the fact that tris(triphenylphosphine)nitratorhodium (I) is reacted with hydrazine in degassed methanol under an inert atmosphere.

2. A process according to claim 1, characterised by the fact that the reaction is carried out under reflux for about 16 hours.

3. A process according to claim 1, characterised by the fact that the inert atmosphere is nitrogen.

4. A process according to claim 1, characterized by the fact that the amount of hydrazine is between 3 and 6 moles per mole of tri(triphenylphosphine)nitratorhodium (I).

5. A process according to claim 4, characterized by the fact that the reaction is carried out under reflux for about 16 hours.

6. A process according to claim 5, characterized by the fact that the inert atmosphere is nitrogen.

7. A process according to claim 6, characterized by the fact that the amount of hydrazine is 4 to 5 moles.

8. A process according to claim 2, characterized by the fact that the inert atmosphere is nitrogen

* * * * *